(12) United States Patent
Huebner et al.

(10) Patent No.: US 8,741,302 B2
(45) Date of Patent: Jun. 3, 2014

(54) **POLYPEPTIDE DERIVED FROM *ENTEROCOCCUS* AND ITS USE FOR VACCINATION**

(75) Inventors: Johannes Huebner, Freiburg (DE); Andrea Kropec-Huebner, Freiburg (DE); Irina Sava, Neufahrn (DE)

(73) Assignee: Universitatsklinikum Freiburg, Freiburg (DE)

( * ) Notice: Subject to any disclaimer, the term of this patent is extended or adjusted under 35 U.S.C. 154(b) by 0 days.

(21) Appl. No.: 13/266,395

(22) PCT Filed: Apr. 26, 2010

(86) PCT No.: PCT/EP2010/002557
§ 371 (c)(1),
(2), (4) Date: Jan. 16, 2012

(87) PCT Pub. No.: WO2010/127784
PCT Pub. Date: Nov. 11, 2010

(65) Prior Publication Data
US 2012/0121638 A1 May 17, 2012

(30) Foreign Application Priority Data
May 5, 2009 (EP) .................................... 09006113

(51) Int. Cl.
*A61K 39/00* (2006.01)
*A61K 39/02* (2006.01)

(52) U.S. Cl.
USPC .................. 424/185.1; 424/190.1; 424/234.1

(58) Field of Classification Search
None
See application file for complete search history.

(56) References Cited

U.S. PATENT DOCUMENTS 4,879,213 A * 11/1989 Fox et al. .......................... 435/5
6,583,275 B1 * 6/2003 Doucette-Stamm et al. 536/23.1

FOREIGN PATENT DOCUMENTS

WO 02/077183 * 10/2002

OTHER PUBLICATIONS

Plotkin et al (Vaccines WB Saunders Company p. 571, 1988).*
Teng et al., "An *Enterococcus faecium* Secreted Antigen, SagA, Exhibits Broad-Spectrum, Binding to Extracellular Matrix Proteins and Appears Essential for *E. faecium* growth", *Infection and Immunity*, 2003, vol. 71, No. 9, pp. 5033-5041.

* cited by examiner

*Primary Examiner* — Albert Navarro
(74) *Attorney, Agent, or Firm* — Saliwanchik, Lloyd & Eisenschenk (57) ABSTRACT

A medicament for the treatment or the prevention of a bacterial infection is disclosed which contains a polypeptide having a contiguous sequence of at least six amino acids of SEQ ID NO:1. Said polypeptide can be used for the preparation of a vaccine against an *Enterococcus* infection.

3 Claims, 6 Drawing Sheets

Fig. 1: Opsonic killing of rabbit serum against E. faecium E155

Fig. 2: Western blot with E155 serum against the homologue strain

1. Molecular weight marker
2. E. faecium E155 cells
3. E. faecium E155 supernatant Fig. 3: Western blot with purified polypeptide having SEQ ID NO:1 lane 1: molecular weight marker
lane 2: partially purified protein
lane 3: purified polypeptide Fig. 4: ELISA with purified polypeptide having SEQ ID NO:1

NSA: rabbit serum before immunization
alpha E155: serum raised against heat-killed bacteria
alpha SEQ ID NO:1 serum raised against recombinant protein Fig. 5: Opsonophagocytic Inhibition with polypeptide having SEQ ID NO:1

Fig. 6: Mouse Bacteremia with E. faecium E155

* unpaired t-test

POLYPEPTIDE DERIVED FROM *ENTEROCOCCUS* AND ITS USE FOR VACCINATION

CROSS REFERENCE TO A RELATED APPLICATION

This application is a National Stage Application of International Application Number PCT/EP2010/002557, filed Apr. 26, 2010; which claims priority to European Patent Application No. 090061116, filed May 5, 2009; which are incorporated herein by reference in their entirety.

Enterococci are among the three most common nosocomial pathogens and due to their multiple antibiotic resistances cause substantial morbidity and mortality, especially among intensive care patients and the immunocompromised. While several new antibiotics have been introduced in the last decade, resistance against these new drugs is developing and spreading rapidly. Life-threatening systemic disease such as endocarditis caused by resistant strains may at times be untreatable. Therefore, alternative treatment and prevention strategies are desperately needed to counter the rise of multiply resistant clones in hospitals and nursing homes worldwide. A better understanding of the different enterococcal cell surface structures will help to target new therapeutic and prophylactic approaches.

It is known that all gram-positive bacteria (also those belonging to the genus of *Enterococcus*) contain in the cell wall several specific carbohydrates and proteins. In the course of the present invention one protein has been identified that plays a possible role in the dynamic equilibrium of a major component of the outer cell wall (i.e. peptidoglycan). Proteins belonging to this family may act as cell wall peptidases which degrade the peptidoglycan of the bacteria during growth and cell division. Surprisingly it has been found that a polypeptide which is probably located on the outer surface of the bacterial cell can be used for the production of vaccines since protective antibodies directed against parts of said polypeptide have been identified.

The humoral immune response is mediated by antibody molecules secreted by plasma cells. Antigen that binds to the B-cell antigen receptor signals B-cells and is at the same time internalized and processed into peptides that activate armed helper T-cells. Signals from the bound antigen and from the helper T-cell induce the B-cell to proliferate and differentiate into plasma cells secreting specific antibody. These antibodies protect the host from infection in three main ways. First, said antibodies can inhibit the toxic effects or infectivity of pathogens by binding to them. Such antibodies are termed neutralizing antibodies.

Second, by coating the pathogens, said antibodies can enable accessory cells that recognize the Fc portions of arrays of antibodies to ingest and kill the pathogen. This process is called opsonisation. Third, antibodies can trigger the activation of the complement system. Complement proteins can strongly enhance opsonisation or can directly kill certain bacterial cells.

For the production of vaccines it is important that the antigen elicits antibodies which inhibit the pathogenic activity of the pathogenic microorganism. Protective antibodies elicited by a vaccine have therefore the effect of neutralization, opsonisation and complement activation whereby antibodies induced by a specific antigen may also have two or even three of the protective activities.

It is therefore one object of the present invention to provide a polypeptide or part thereof which can be used to produce protective antibodies, preferably IgG antibodies against said polypeptide or parts of said polypeptide.

The present invention provides therefore a polypeptide having the following amino acid sequence:

```
(SEQ ID NO: 1)
MKKSLISAVMVCSMTLTAVASPIAAAADDFDSQIQQQDQKIADLKNQQADAQSQID

ALESQVSEINTQAQDLLAKQDTLRQESAQLVKDIADLQERIEKREDTIQKQAREAQV

SNTSSNYIDAVLNADSLADAIGRVQAMTTMVKANNDLMEQQKQDKKAVEDKKAE

NDAKLKELAENQAALESQKGDLLSKQADLNVLKTSLAAEQATAEDKKADLNRQK

AEAEAEQARIREQQRLAEQARQQAAQEKAEKEAREQAEAEAQATQASSTAQSSAT

EESSATQSSMTEESSSATQSSATEESTTPESSTEESTAPESSATEESTTAPESSATEEST

TVPESSATEESTTVPESSTTEESTTPAPTTPSTDQSVDTGNGTGSSTPAPTPTPTPEQP

KPVTPAPAPSGSVNGAAIVAEAYKYIGTPYVWGGKDPSGFDCSGFTRYVYMQVTG

RDIGGWTVPQESAGTKISVSQAKAGDLLFWGSQGGTYHVAIALGGGQYIHAPQPG

ESVKVGSVQWFAPDFAVSM
```

Fang Teng et al. (in: Fang Teng et al. An *Enterococcus faecium* Secreted Antigen, SagA, Exhibits Broad-Spectrum Binding to Extracellular Matrix Proteins and Appears Essential for *E. faecium* Growth, Infection and Immunity, September 2003, p. 5033-5041, Vol. 71, No. 9) discloses the extracellular and secreted *E. faecium* SagA protein as apparently essential for growth, showing broad-spectrum binding to ECM proteins, forming oligomers, and antigenic during infection. Furthermore, antibodies produced against recombinant Sag A are described. Although the protein is described as secreted antigen, there is no disclosure of an actual antigenicity of Sag A in vivo, let alone the formation of opsonic and/or protective antibodies in a host. The publication merely describes a C-terminal domain of Sag A that is "similar to that found in various proteins", including P60 (52% similarity) of *L. monocytogenes*, which has cell wall hydrolase activity, and has also been shown to be involved in virulence. The publication is thus limited to the functional characterization of Sag A.

Furthermore, the presence of a surface-exposed proteins does not automatically result in the formation of opsonic and/or protective antibodies in the host. In fact, to the knowledge of the inventors, only two protein antigens have been confirmed so far in *E. faecalis* as being the target of protective antibodies: an ABC transporter described by Burnie and colleagues (Burnie et al. Identification of ABC transporters in vancomycin-resistant *Enterococcus faecium* as potential targets for antibody therapy. FEMS Immunol Med Microbiol (2002) vol. 33 (3) pp. 179-89) and, only recently, the collagen adhesin ACE (Singh et al. Importance of the collagen adhesin ace in pathogenesis and protection against *Enterococcus faecalis* experimental endocarditis. PLoS Pathog (2010) vol. 6(1) pp. e1000716). Two other surface proteins have been shown to be not protective, namely the enterococcal aggregation substance (McCormick et al. Antibodies to a surface-exposed, N-terminal domain of aggregation substance are not protective in the rabbit model of *Enterococcus faecalis* infective endocarditis. Infect Immun (2001) vol. 69 (5) pp. 3305-14) and the enterococcal surface protein Esp (Sava et al., submitted). Studies on several other protein antigens have been reported in the literature as being involved in virulence, while no protective effect of either passive or active immunization has been documented. Therefore, to date, no vaccine targets, either proteinaceous or carbohydrates, have been identified in *E. faecium*. The present invention is therefore based on the surprising finding that the polypeptide of SEQ ID NO:1 can be used to provide such a vaccine target.

The person skilled in the art knows that not necessarily the whole polypeptide has to be used for the production of a vaccine. Even shorter fragments of the polypeptide can be used. Such fragments comprise an epitope that usually consist of at least six contiguous amino acids out of the SEQ ID NO:1. Preferably, however, said polypeptides have at least 10, more preferably at least 15 and more preferred at least 20 contiguous amino acids of the SEQ ID NO:1.

In a particularly preferred embodiment the polypeptide has at least 30, more preferred at least 50 and especially preferred at least 100 contiguous amino acids of SEQ ID NO:1.

The person skilled in the art is aware that with suitable computer programs the hydrophobicity and hydrophilicity of the areas of the polypeptide can be determined. Therefore, the preferred fragments are mainly hydrophilic since the parts of the polypeptide which are located on the outer areas of the folded polypeptide are preferred for the preparation of a vaccine.

Moreover, when longer parts of the polypeptide are used, it is more likely that not only linear epitopes are within the fragment but also conformational epitopes are present which occur in the course of three-dimensional folding of the polyprotein.

In a preferred embodiment the polypeptide of SEQ ID NO:1 or a fragment thereof is used as conjugate, whereby the antigen is covalently bound to an immunocarrier. Such immunocarrier may be a polypeptide or a protein or a carbohydrate-containing molecule (such as for example a capsular polysaccharide or glycoconjugate) which improves the interaction between T- and B-cells for the induction of an immune response against the antigen. This may be preferred for vaccines intended for use in patients with reduced activity of the immune system. Since infections of Enterococci are frequently a problem in hospitals and nursing homes such conjugates are particularly preferred for such patients. Suitable immunocarriers according to the present invention comprise tetanus toxoid, diphtheria toxoid, *Pseudomonas aeruginosa* toxin A or its derivatives thereof.

Carbodydrate-containing molecules such as capsular polysaccharides or teichoic acids may also serve as conjugation partner for the above-mentioned polypeptide or fragments thereof. In an especially preferred embodiment such fragments of the immunocarrier are used which stimulate the immune response in the patient to be treated without having, however, the undesired side effect which such proteins may elicit when used in an unmodified form.

The covalent bond between the antigen and the immunocarrier can be provided by a direct chemical bond or by a spacer. Sometimes short molecules having two reactive groups on both ends are reacted with the antigen and the immunocarrier in order to produce a covalently linked molecule.

In an alternative the molecule used as vaccine (antigen and immunocarrier) can be produced recombinantly wherein suitable gene fragments are linked together and inserted into a appropriate vector. The vector is introduced in a suitable host cell and the host cell (e.g. *E. coli*, bacillus, yeast, or insect cells) produces the polypeptide or fragment thereof as defined above together with the immunocarrier as one molecule.

The polypeptide or fragment thereof either alone or coupled to an immunocarrier may be used for the treatment or the prevention of bacterial infections. Another aspect of the present invention thus is a method for the treatment or the prevention of bacterial infections, in particular of Enterococci, more preferably *Enterococcus faecium* based on the medicament as described herein. Said medicament preferably is a vaccine which comprises preferably also a pharmaceutically acceptable adjuvant. The adjuvant promotes the protective IgG subtype antibodies. Typical adjuvants include complete Freund's adjuvant (CFA), incomplete Freund's adjuvant (IFA), alum and other adjuvants suitable for human use (e.g. virus-like particles). Polymers like dextran sulfate have been shown to be also a potent stimulator of IgG antibodies against bacterial cell surface antigen.

An active vaccine is administered to the patient preferably before an infection occurs. Such vaccination can therefore be applied regularly to patients at risk (e.g. elderly people, patients before solid organ or bone-marrow transplants) in order to stimulate their immune response and to avoid an infection in a hospital or a nursing home.

Under specific circumstances it may, however, also be possible to apply the vaccine at early stages of the infection in order to elicit protective antibodies which inactivate the bacteria belonging to the genus *Enterococcus*. In a preferred embodiment the vaccine of the present invention provides protection against different *Enterococcus faecium* and possibly also against *Enterococcus faecalis* strains since there is extensive sequence homology between these species.

Antibodies induced by the protein of SEQ ID NO:1 or suitable fragments thereof are protective and facilitate phagocytosis. Since such protective, and in particular opsonic antibodies, are preferred it is desired to use those parts of the polypeptide of SEQ ID NO:1 which elicit antibodies having opsonic properties.

The pharmaceutical formulation of a medicament to be used as a vaccine is known to the person skilled in the art, and described in the respective literature. Usually, a solution of the antigen possibly coupled to an immunocarrier is dissolved in a physiologically acceptable solution like a buffer. The solution must be stabilized in order to avoid an undesired precipitation of the immunologically active compounds. The vaccine is preferably produced in the form of a solution adapted to injection, preferably intramuscular injection. Other forms of pharmaceutical formulations like plasters or sprays are also acceptable provided the antigen comes in sufficient contact with the immune system and the formation of specific antibodies is elicited.

On the other hand, it is sometimes not possible to treat patients with an active vaccine since the immune system is severely impaired. In those circumstances the polypeptide of SEQ ID NO:1 or fragments thereof as defined above can be used to produce either polyclonal antibodies or monoclonal antibodies that bind to or opsonize *Enterococcus*. The person skilled in the art is well aware how such antibodies can be prepared.

The inoculum for polyclonal antibody production is typically prepared by dispersing the antigen or the antigen-immunocarrier conjugate in a physiologically tolerable diluent such as saline, to form an aqueous composition. An immunostimulatory amount of the inoculum preferably with adjuvant is administered to a mammal and the inoculated mammal is then maintained for a time period sufficient for the antigen to induce protective anti-*Enterococcus* antibodies. After suitable periods of time, two weeks until four months, boosting doses of the antigen-immunocarrier may be applied and the antigen titer is monitored. At a suitable point, when the titer of the neutralizing or opsonic antibodies is at its peak, the antibodies are collected. Such antibodies can include antibody preparations from a variety of commonly used animals (such as mice, goats, primates, donkeys, rabbits or horses) and humans, whereby the antibodies are isolated from blood donations.

The antibodies induced in the mammal are harvested, isolated and purified to the extent desired by well-known techniques such as by alcohol fractionation and column chromatography or preferably by immunoaffinity chromatography whereby the antigen is bound to a chromatographic column. The antiserum passes the column whereby specific antibodies are retained and all other components of the serum are washed out. Then the purified antibodies are eluted with suitable gradients. A further purification may be required.

Alternatively, monoclonal antibodies can be prepared according to techniques well-known to the person skilled in the art. When a suitable monoclonal antibody is obtained, the binding regions can be identified and the whole antibody molecule as well as derivatives of the antibody like antibody fragments or subfragments can be provided. The general technique to produce monoclonal antibodies is amply described in textbooks. After having made the hybridomas or having selected the monoclonal antibody from libraries or genetically engineered animals it has to be determined to which part of the polypeptide of SEQ ID NO:1 the mAb binds. Then, it has to be checked whether the antibody is opsonic and/or protective, preferably in vivo.

The term antibody furthermore includes recombinant antibodies, such as recombinant human and humanized antibodies, as well as (recombinant) antibody fragments, such as scFv-fragments.

The present invention will now be described further in the following examples with reference to the accompanying Figures and the Sequence Listing, nevertheless, without being limited thereto. For the purposes of the present invention, all references as cited herein are incorporated by reference in their entireties.

DESCRIPTION OF THE FIGURES

FIG. 3 is a Western Blot with a recombinantly expressed and purified polypeptide having SEQ ID NO:1. The purified polypeptide has been originally derived from strain *Enterococcus faecium* E155. Using appropriate primers the gene has been amplified by PCR and cloned into an expression vector for gram-negative bacteria. The protein produced by the host cells has been purified with a Ni-column through a His-Tag. The purified protein was used for the production of polyclonal antibodies in rabbits. The antibodies were used in the Western Blot as shown in FIG. 3 and tested for opsonic activity. The specificity or the opsonic antibodies has been confirmed by absorption with the purified protein.

SEQ ID NO:1 shows the amino acid sequence of the polypeptide according to the invention derived from strain *Enterococcus faecium* E155.

EXAMPLE 1

Figure 1:
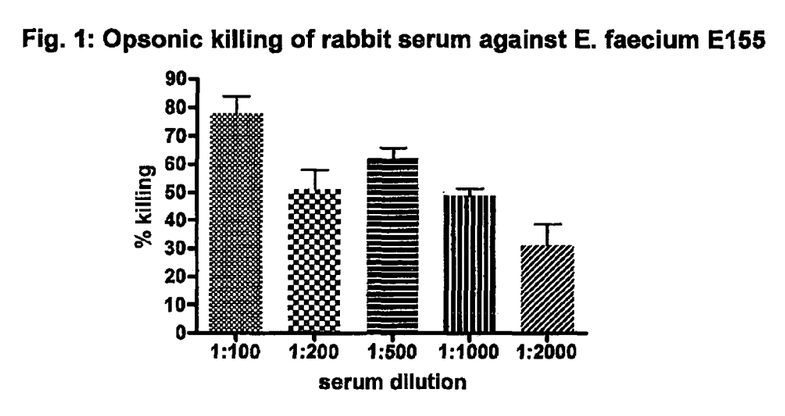
FIG. 1 shows opsonic killing of a polyclonal antiserum produced in rabbits against the strain *Enterococcus faecium* E155. Different serum dilutions were tested and even at high dilutions a substantial opsonic activity of the raised antibodies could be observed.

In an attempt to identify targets of opsonic antibodies in *E. faecium* a rabbit was immunized with heat-killed *E. faecium* strain E155 [Leavis, H. L. et al. (2007). Insertion sequence-driven diversification creates a globally dispersed emerging multiresistant subspecies of *E. faecium*. PLoS Pathog 3:e7] belonging to the clonal complex 17 (CC17) that is associated with hospital outbreaks of vancomycin-resistant enterococci (VRE) [Top, J. et al., (2008). Emergence of CC17 *Enterococcus faecium*: from commensal to hospital-adapted pathogen. FEMS Immunol Med Microbiol 52:2997-308]. Bacteria were heat-killed at 65° C. for 1 hour and a final concentration of $1.4 \times 10^{12}$ cfu/dose was injected i.v. 3 times per week for a total of 3 weeks. The resulting sera were opsonic against the homologous strain (77.8% killing at a serum-dilution 1:100). The results are shown in FIG. 1.

EXAMPLE 2

Figure 2:
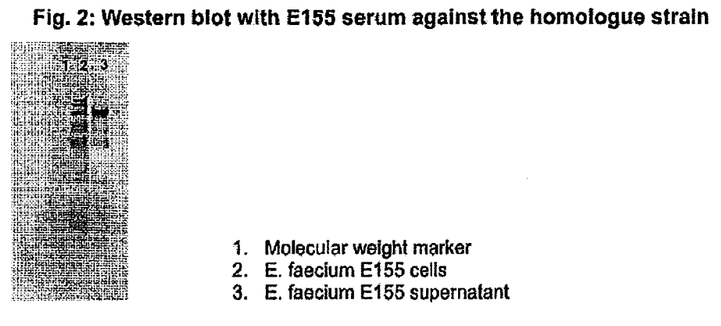
FIG. 2 shows a Western Blot of antibodies against *Enterococcus faecium* strain E155 reacted with proteins derived from the homologous strain. Lane 1 is a molecular weight marker. In lane 2 a lysate of *E. faecium* E155 cells was applied. In lane 3 the supernatant of *E. faecium* E155 culture was applied.

Western blot analysis showed a distinct protein band of ca. 54 kDa that was present in cellular extracts and even more pronounced in the culture supernatant. (The results are shown in FIG. 2).

EXAMPLE 3

All five tested *E. faecium* strains expressed a protein band of the same size that was detected by the immune rabbit serum (data not shown). Nano LC-ES-MS/MS analysis of the Coomassie blue stained gel band resulted in sequence data that were compared to NCBI and MASCOT databases. The highest homology (score 1253) was obtained with NLP/P60, a 55 kDa protein from *E. faecium* DO (Accession No Gi|69245436) [Anantharaman, V. et al. (2003). Evolutionary history, structural features and biochemical diversity of the NlpC/P60 superfamily of enzymes. Genome Biol 4:R11].

Figure 3:
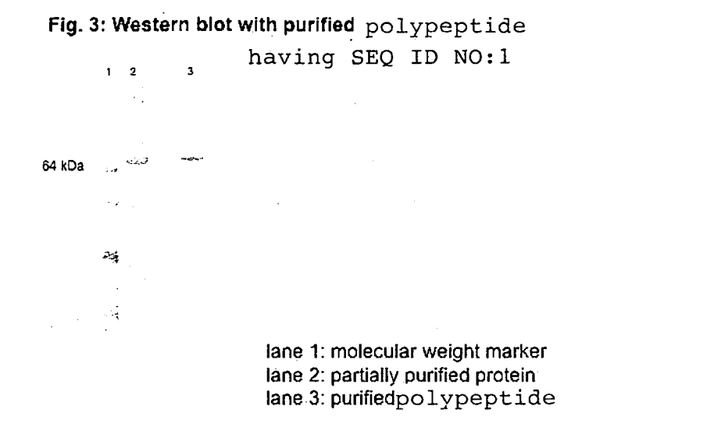

The gene was subsequently amplified from *E. faecium* E155 by PCR and cloned into a his-tag expression vector (Champion pET Directional TOPO Expression Kit, Invitrogen). The expressed protein was purified on nickel columns under denaturing conditions and the purified protein was shown to be reactive with the rabbit sera raised against whole E. faecium E155 cells. (The results are shown in FIG. 3).

EXAMPLE 4

Figure 4:
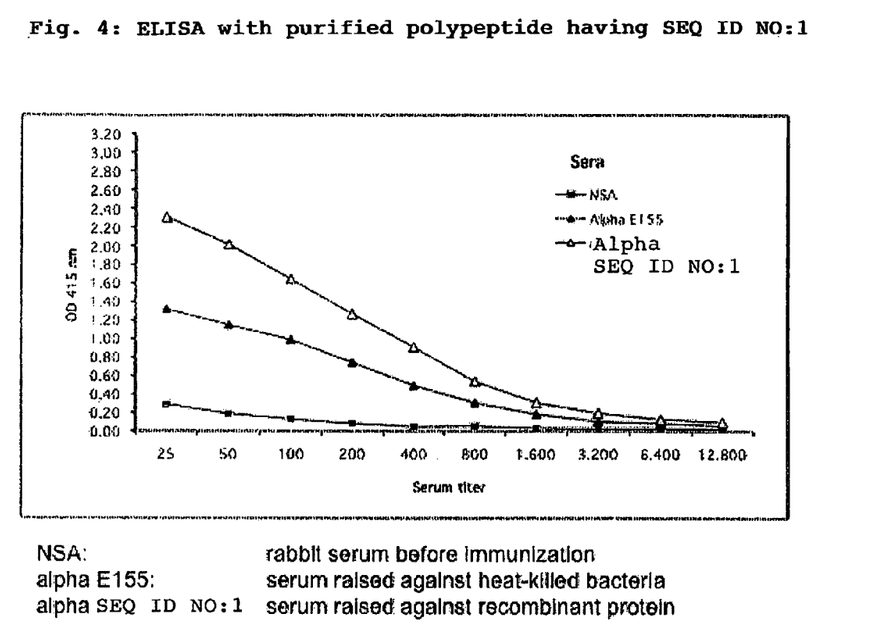
FIG. 4 shows the results of an ELISA test performed with the purified polypeptide having SEQ ID NO:1 and in comparison thereto with serum raised against heat-inactivated bacteria (alpha E155) and normal rabbit serum (NSA).

A rabbit was immunized with the purified protein (2 times 10 μg subcutaneous (SC) mixed with incomplete Freud's adjuvant and given 2 weeks apart and in the third week 3 times 5 μg IV) without adjuvant. Two weeks after the last injection, titers were checked by ELISA (see FIG. 4), and by opsonophagocytic assay (see FIG. 5).

EXAMPLE 5

Figure 5:
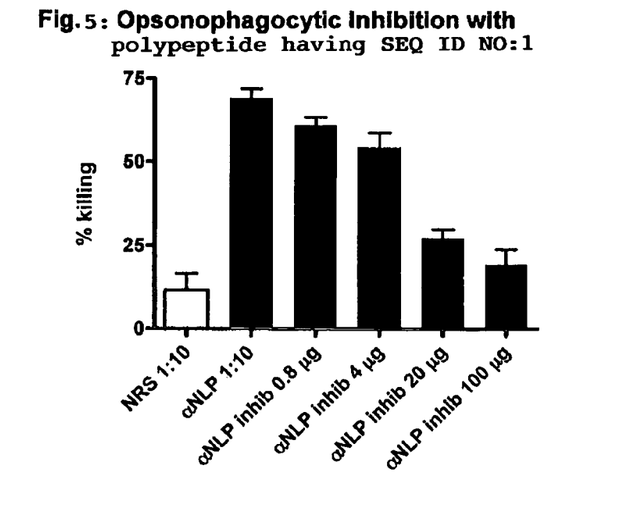
FIG. 5 shows the results of the opsonophagocytic inhibition obtained with the polypeptide having SEQ ID NO:1.
Figure 6:
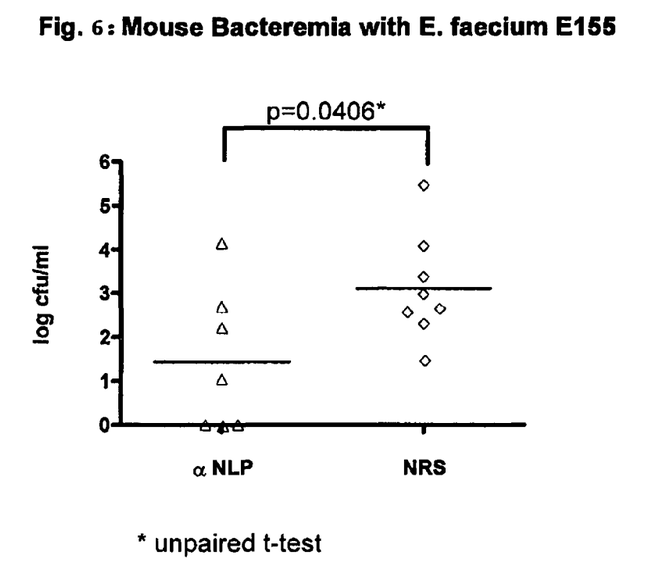
FIG. 6 shows the Mouse bacteraemia model using *E. faecium* E155, comparing the effects of serum raised against purified SagA protein (αNLP, triangles) with normal rabbit serum (NRS, diamonds), using colony counts in the blood. Statistical analysis was done by Students t-test; horizontal lines indicate the median.

To confirm specificity an opsonophagocytic inhibition assay was done showing that 100 μg of purified protein was able to inhibit killing by almost 100%, while lower amounts inhibited killing in a dose-depended fashion (see FIG. 5). The opsonophagocytic assay was done as described elsewhere [Theilacker, C. et al. Opsonic antibodies to Enterococcus faecalis strain 12030 are directed against lipoteichoic acid. Infect Immun (2006) 74: 5703-12]. In brief, baby rabbit serum (1:15 dilution), human PMNs, and appropriate serum dilutions were mixed with bacteria grown to logarithmic phase (ration bacteria to PMNs 1:1). The mixture was incubated on a rotor rack at 37° C. After 90 min leukocytes were lysed and appropriate dilutions were plated onto tryptic soy agar plates. The plates were incubated over night and colonies were counted the following day.

In summary, these data confirm that the polypeptide having SEQ ID NO:1 from E. faecium is a vaccine candidate inducing opsonic antibodies against clinical isolates of vancomycin-resistant E. faecium.

EXAMPLE 6

Protective efficacy of antibodies against polypeptide having SEQ ID NO:1 was shown in a mouse bacteremia model. Female balb/c mice (8 mice per group) received 200 μl normal rabbit serum (NRS) or serum raised against polypeptide having SEQ ID NO:1 (IRS). The animals were challenged with E. faecium E155 after 24 hours ($1.18 \times 10^{10}$ cfu/mouse) and received a second dose of 200 μl rabbit serum (either NRS or IRS) 2 h after inoculation. Mice were sacrificed 8 hours after infection and colony counts in the blood were determined. These results show a statistically significant reduction on colony counts from blood when mice received IRS.

E. faecium possesses a cell-surface associated protein of approximately 54 kD that is secreted into the culture medium and induces specific antibodies in rabbits immunized with heat-killed E. faecium. The protein was identified by Nano LC-ES-MS/MS analysis, amplified by PCR, and cloned into a gram-negative expression vector. Purified recombinant protein was used to immunize a rabbit and the resulting antiserum was shown by ELISA to bind specifically to the protein. Rabbit sera killed the homologous strain >50% at a serum dilution of 1:10 and the killing activity could be completely absorbed with the purified antigen. Two applications of serum (24 h before and 2 h after inoculation) statistically reduced colony counts in the blood of mice confirming that this antigen is a promising vaccine target for vancomycin resistant Enterococcus (VRE) bacteremia.

The invention claimed is:

1. A method for eliciting an immune response in a human subject, wherein said method comprises administering, to a subject in the need of such an immune response, a polypeptide comprising SEQ ID NO:1, and wherein said eliciting an immune response comprises the generation of opsonic antibodies against *Enterococcus*.

2. The method according to claim 1 wherein the polypeptide is covalently bound to an immunocarrier.

3. The method according to claim 1 wherein said immune response is against *Enterococcus faecium* or *E. faecalis*.

* * * * *

UNITED STATES PATENT AND TRADEMARK OFFICE
CERTIFICATE OF CORRECTION

| | | |
|---|---|---|
| PATENT NO. | : 8,741,302 B2 | Page 1 of 1 |
| APPLICATION NO. | : 13/266395 | |
| DATED | : June 3, 2014 | |
| INVENTOR(S) | : Johannes Huebner et al. | |

It is certified that error appears in the above-identified patent and that said Letters Patent is hereby corrected as shown below:

In the Specification

<u>Column 1,</u>
Line 11, "Application No. 090061116" should read -- Application No. 09006113.6 --.

Signed and Sealed this
Eleventh Day of November, 2014

Michelle K. Lee
*Deputy Director of the United States Patent and Trademark Office*

SEQUENCE LISTING

```
<160> NUMBER OF SEQ ID NOS: 1

<210> SEQ ID NO 1
<211> LENGTH: 524
<212> TYPE: PRT
<213> ORGANISM: Enterococcus faecium

<400> SEQUENCE: 1

Met Lys Lys Ser Leu Ile Ser Ala Val Met Val Cys Ser Met Thr Leu
1               5                   10                  15

Thr Ala Val Ala Ser Pro Ile Ala Ala Ala Ala Asp Asp Phe Asp Ser
            20                  25                  30

Gln Ile Gln Gln Gln Asp Gln Lys Ile Ala Asp Leu Lys Asn Gln Gln
        35                  40                  45

Ala Asp Ala Gln Ser Gln Ile Asp Ala Leu Glu Ser Gln Val Ser Glu
    50                  55                  60

Ile Asn Thr Gln Ala Gln Asp Leu Leu Ala Lys Gln Asp Thr Leu Arg
65                  70                  75                  80

Gln Glu Ser Ala Gln Leu Val Lys Asp Ile Ala Asp Leu Gln Glu Arg
            85                  90                  95

Ile Glu Lys Arg Glu Asp Thr Ile Gln Lys Gln Ala Arg Glu Ala Gln
            100                 105                 110

Val Ser Asn Thr Ser Ser Asn Tyr Ile Asp Ala Val Leu Asn Ala Asp
        115                 120                 125

Ser Leu Ala Asp Ala Ile Gly Arg Val Gln Ala Met Thr Thr Met Val
    130                 135                 140

Lys Ala Asn Asn Asp Leu Met Glu Gln Gln Lys Gln Asp Lys Lys Ala
145                 150                 155                 160
```

-continued

```
Val Glu Asp Lys Lys Ala Glu Asn Asp Ala Lys Leu Lys Glu Leu Ala
                165                 170                 175

Glu Asn Gln Ala Ala Leu Glu Ser Gln Lys Gly Asp Leu Leu Ser Lys
            180                 185                 190

Gln Ala Asp Leu Asn Val Leu Lys Thr Ser Leu Ala Ala Glu Gln Ala
            195                 200                 205

Thr Ala Glu Asp Lys Lys Ala Asp Leu Asn Arg Gln Lys Ala Glu Ala
            210                 215                 220

Glu Ala Glu Gln Ala Arg Ile Arg Glu Gln Gln Arg Leu Ala Glu Gln
225                 230                 235                 240

Ala Arg Gln Gln Ala Ala Gln Glu Lys Ala Glu Lys Glu Ala Arg Glu
            245                 250                 255

Gln Ala Glu Ala Glu Ala Gln Ala Thr Gln Ala Ser Ser Thr Ala Gln
            260                 265                 270

Ser Ser Ala Thr Glu Glu Ser Ser Ala Thr Gln Ser Ser Met Thr Glu
            275                 280                 285

Glu Ser Ser Ser Ala Thr Gln Ser Ser Ala Thr Glu Glu Ser Thr Thr
    290                 295                 300

Pro Glu Ser Ser Thr Glu Glu Ser Thr Ala Pro Glu Ser Ser Ala Thr
305                 310                 315                 320

Glu Glu Ser Thr Thr Ala Pro Glu Ser Ser Ala Thr Glu Glu Ser Thr
                325                 330                 335

Thr Val Pro Glu Ser Ser Ala Thr Glu Glu Ser Thr Thr Val Pro Glu
            340                 345                 350

Ser Ser Thr Thr Glu Glu Ser Thr Thr Pro Ala Pro Thr Thr Pro Ser
            355                 360                 365

Thr Asp Gln Ser Val Asp Thr Gly Asn Gly Thr Gly Ser Ser Thr Pro
    370                 375                 380

Ala Pro Thr Pro Thr Pro Thr Pro Glu Gln Pro Lys Pro Val Thr Pro
385                 390                 395                 400

Ala Pro Ala Pro Ser Gly Ser Val Asn Gly Ala Ala Ile Val Ala Glu
                405                 410                 415

Ala Tyr Lys Tyr Ile Gly Thr Pro Tyr Val Trp Gly Gly Lys Asp Pro
            420                 425                 430

Ser Gly Phe Asp Cys Ser Gly Phe Thr Arg Tyr Val Tyr Met Gln Val
            435                 440                 445

Thr Gly Arg Asp Ile Gly Gly Trp Thr Val Pro Gln Glu Ser Ala Gly
    450                 455                 460

Thr Lys Ile Ser Val Ser Gln Ala Lys Ala Gly Asp Leu Leu Phe Trp
465                 470                 475                 480

Gly Ser Gln Gly Gly Thr Tyr His Val Ala Ile Ala Leu Gly Gly Gly
            485                 490                 495

Gln Tyr Ile His Ala Pro Gln Pro Gly Glu Ser Val Lys Val Gly Ser
            500                 505                 510

Val Gln Trp Phe Ala Pro Asp Phe Ala Val Ser Met
            515                 520
```